Figure 15:
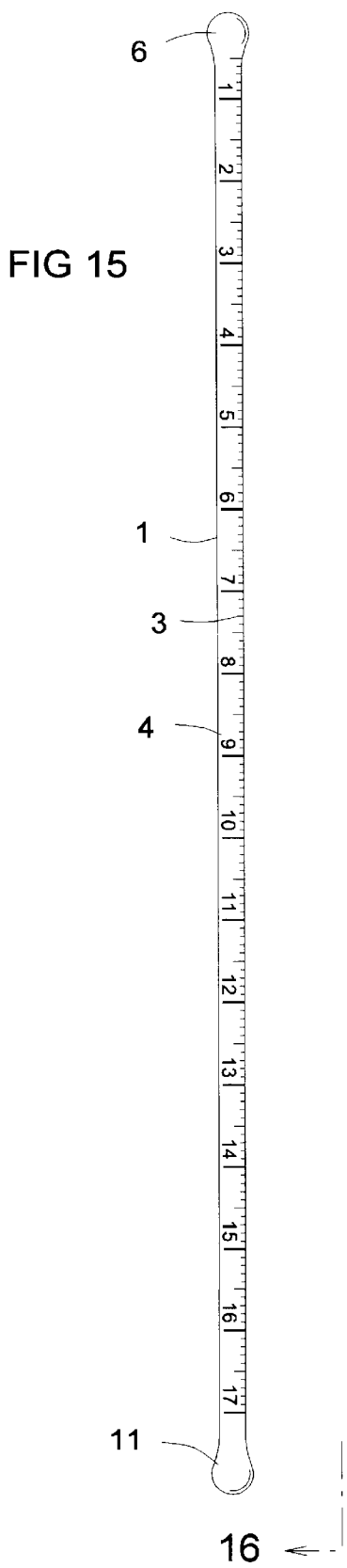

United States Patent [19]
Davis

[11] Patent Number: 5,807,280
[45] Date of Patent: Sep. 15, 1998

[54] PRESSURE ULCER MEASUREMENT PROBE AND METHOD

[75] Inventor: Diane Marie Davis, Redlands, Calif.

[73] Assignee: Linda Sue Mangels, Apopka, Fla.

[21] Appl. No.: 806,092

[22] Filed: Feb. 25, 1997

[51] Int. Cl.⁶ .................................................. A61B 5/103
[52] U.S. Cl. .................................. 600/587; 604/1; 33/511
[58] Field of Search ................................. 600/582, 583, 600/590; 604/1, 2, 3; 33/511–515

[56] References Cited

U.S. PATENT DOCUMENTS

| | | | |
|---|---|---|---|
| 977,825 | 12/1910 | Murphy | 604/1 |
| 1,652,108 | 12/1927 | Forbis | 604/1 |
| 4,226,025 | 10/1980 | Wheeler | 600/587 |
| 5,090,902 | 2/1992 | Lemon et al. | 433/72 |
| 5,137,447 | 8/1992 | Hunter | 433/72 |
| 5,171,248 | 12/1992 | Ellis | 600/587 |
| 5,423,677 | 6/1995 | Brattesani | 433/72 |
| 5,578,018 | 11/1996 | Rowland et al. | 600/569 |

*Primary Examiner*—Max Hindenberg
*Assistant Examiner*—Pamela L. Wingood
*Attorney, Agent, or Firm*—John V. Stewart

[57] ABSTRACT

A shaft (1) having a fiber swab (5) on one end, a metric scale (2) on the shaft starting at the swab end, and preferably a flat portion (7) of the shaft for orienting the scale by touch, without visual inspection. A second scale (3) is preferably provided, starting at the opposite end from the first scale, and on the opposite side of the shaft. The shaft optionally includes a bulb (6) on one or both ends. An arrangement of tactile indicators (7 and 8) allows a practitioner to orient the probe for used of the desired end and its associated scale by touch alone, allowing visual concentration on the patient.

13 Claims, 4 Drawing Sheets

FIG 1
FIG 2
FIG 3
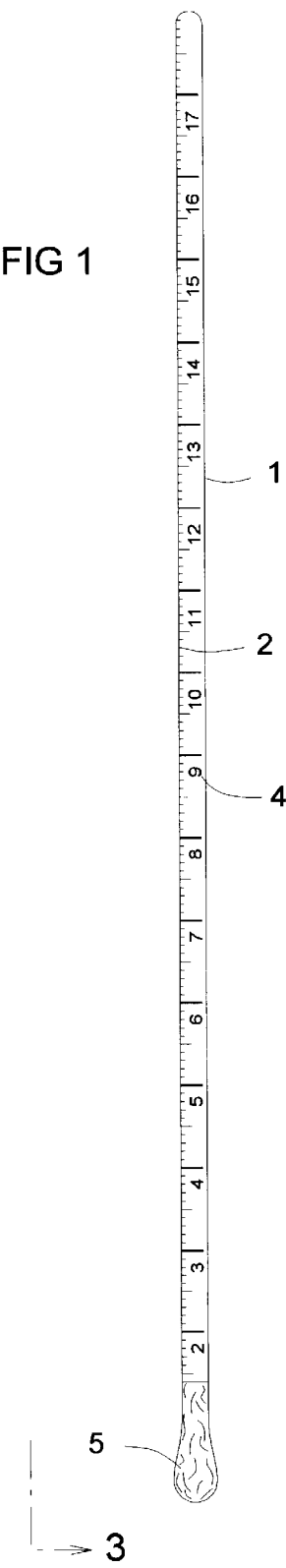
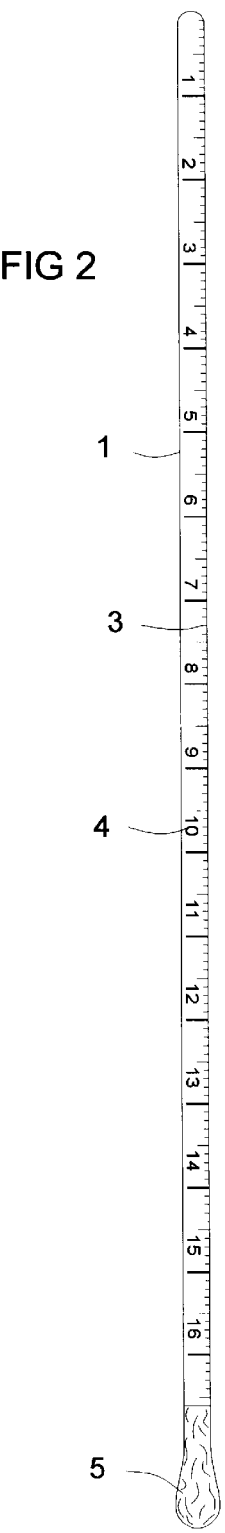
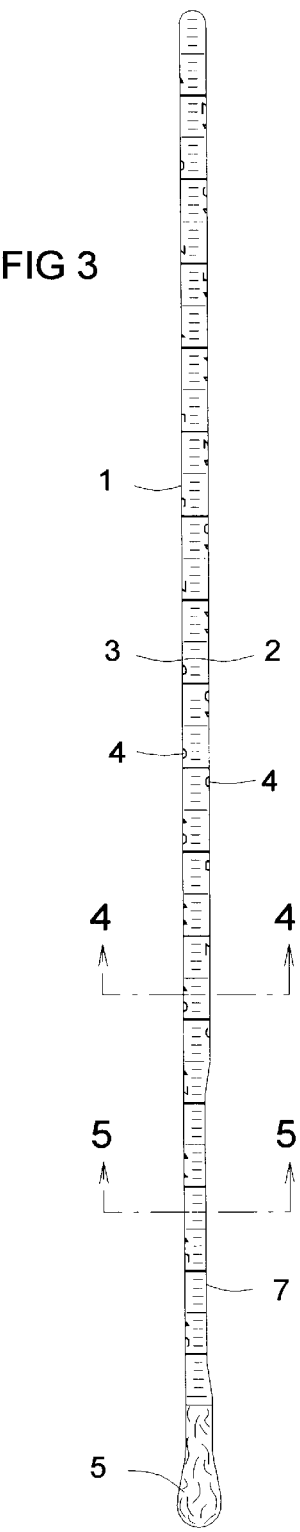

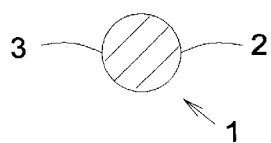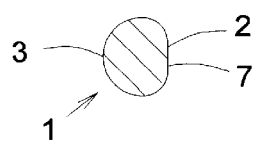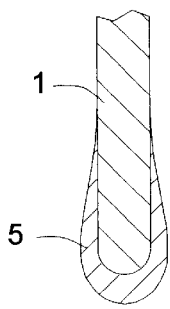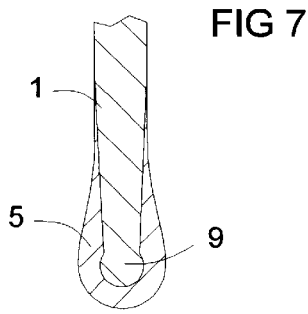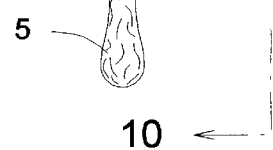

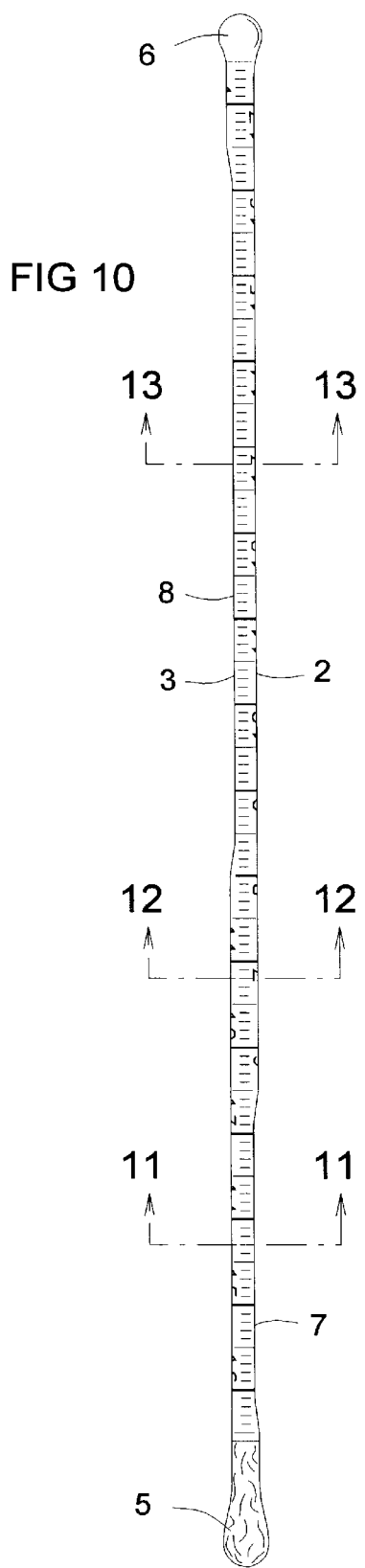
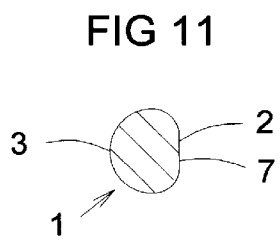
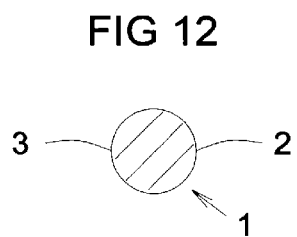
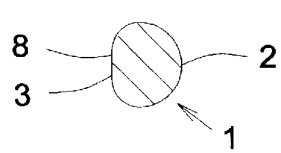
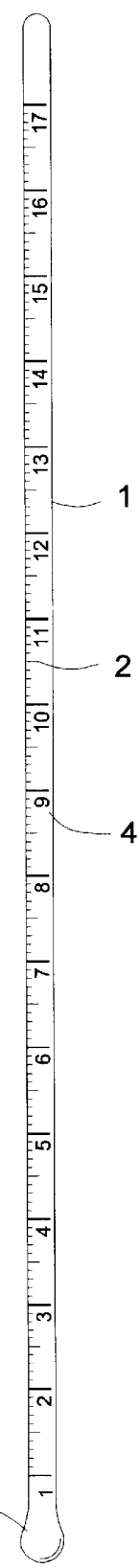

PRESSURE ULCER MEASUREMENT PROBE AND METHOD

BACKGROUND

1. Field

This invention relates to devices and methods for measuring the surface dimensions and depths of pressure ulcers (bed sores).

2. Prior Art

Current practice for measuring the dimensions of pressure ulcers is to use a small-diameter shaft about 15–20 cm long, having a fiber swab on one end. The shaft is laid diametrically across the surface of an ulcer, with the swab touching the perimeter of the ulcer. The practitioner grips the shaft where it crosses the opposite perimeter, places the shaft on a metric scale, and reads the distance from the swab to the grip point. This process is repeated perpendicularly to the first measurement, giving a width and height estimation of the ulcer. The swab end of the shaft is then inserted into the ulcer until it stops at the bottom of the ulcer. The practitioner grips the shaft at the skin surface level, and places the shaft on a scale as before, to determine the depth of the ulcer. The shaft may need to be inserted deeply into "tunnels" of the ulcer, extending just below the skin surface, so that the depth of each tunnel is obtained. The devices now used for this practice, including fiber-tipped swabs and metric scales, are discarded after each patient, and are very inexpensive.

Disadvantages of the current practice include the time spent in moving the shaft to a metric scale, the resultant spread of ulcer fluids, the dexterity and effort required to set and maintain a precise grip, inaccuracy from loss of grip position, and the need to manage more than one device at the same time.

Related devices are periodontal probes for measuring the depth of gingival pockets in gums of the mouth. Examples are shown in U.S. Pat. Nos. 5,423,677, 5,137,447 and 5,090,092. However, these are not suitable for measuring the dimensions and depths of pressure ulcers, or for general medical measurements.

SUMMARY

An object of this invention is to provide a pressure ulcer measurement probe that is directly readable, eliminating the need for a separate scale and the steps of holding the shaft at a precise location and moving it to a scale for reading. Other objects include improved safety, reduced measurement time, reduced distraction, probe tip options, and disposability.

It will be seen that these objects are met in the present invention. It is a probe for measuring the surface dimensions and depths of pressure ulcers (bed sores), comprising a shaft (1) having a fiber swab (5) on one end, a metric scale (2) on the shaft starting at the swab end, and preferably a flat portion (7) of the shaft for orienting the scale by touch, without visual inspection. A second scale (3) is preferably provided, starting at the opposite end from the first scale, and on the opposite side of the shaft. The shaft optionally includes a bulb (6) on one or both ends. An arrangement of tactile indicators (7 and 8) allows a practitioner to orient the probe for used of the desired end and its associated scale by touch alone, allowing visual concentration on the patient.

DRAWINGS

FIG. 1 Front view of probe showing first scale (2)

FIG. 2 Back view of probe showing second scale (3)

FIG. 3 Side view of probe taken along view line 3 of FIG. 1

FIG. 4 Enlarged sectional view of shaft taken along line 4—4 of FIG. 3

FIG. 5 Enlarged sectional view of shaft taken along line 5—5 of FIG. 3

FIG. 6 Enlarged sectional view of fiber swab on end of shaft

FIG. 7 Enlarged sectional view of fiber swab on end of shaft with retention end

FIG. 8 Front view of probe with swab (5) on first end, bulb (6) on second end

FIG. 9 Back view of probe of FIG. 8, showing second scale (3)

FIG. 10 Side view of probe taken along view line 10 of FIGS. 8 and 9

FIG. 11 Enlarged sectional view of shaft taken along line 11—11 of FIG. 10

FIG. 12 Enlarged sectional view of shaft taken along line 12—12 of FIG. 10

FIG. 13 Enlarged sectional view of shaft taken along line 13—13 of FIG. 10

FIG. 14 Front view of probe with bulb on first end

FIG. 15 Back view of probe with bulb on both ends

Figure 16:
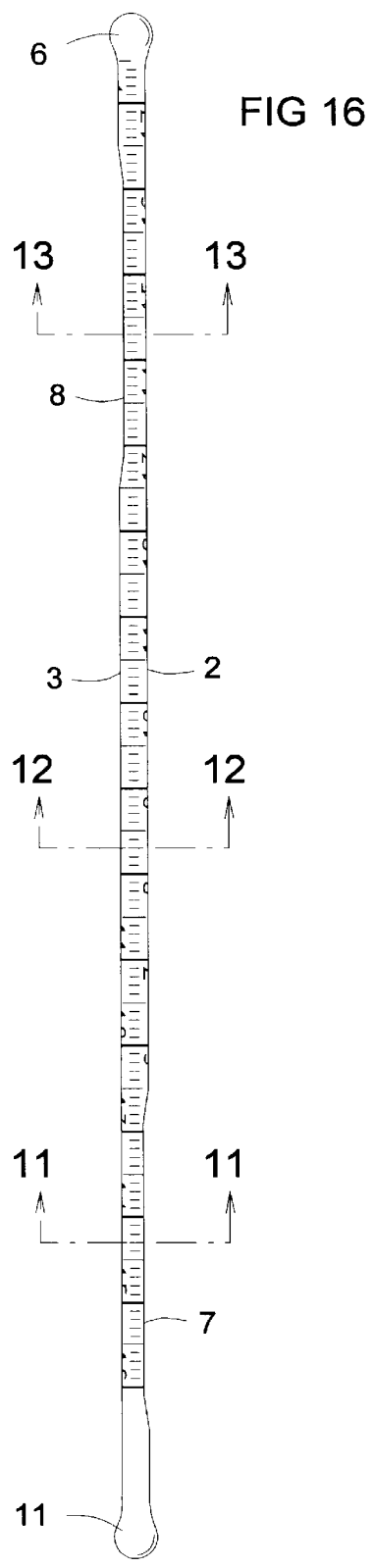

FIG. 16 Side view of probe taken along view line 16 of FIG. 15

Figure 17:
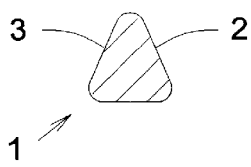

FIG. 17 Optional generally triangular cross section of shaft

REFERENCE NUMERALS

1. Shaft of probe
2. First scale on shaft, for measurements from first end of probe
3. Second scale on shaft, for measurements from second end of probe
4. Numbers on scale, indicating units
5. Fiber swab on first end of probe
6. Bulb on second end of probe
7. First flat portion of shaft
8. Second flat portion of shaft
9. Safety retention contour on first end of shaft for retaining the swab
11. Bulb on first end of probe

DESCRIPTION

FIGS. 1–6 show a first embodiment of the invention. A shaft (1) has a fiber swab (5) on one end and a first metric scale (2) along the shaft starting from the swab end. FIG. 2 shows the opposite side of FIG. 1, with an optional second scale (3) starting from the end opposite the swab. The swab covers an initial portion of the first scale, so a second scale is useful for measurements shorter than the swab, or where a swab is not wanted. FIG. 3 shows a view of FIG. 1 when rotated 90 degrees about the shaft axis. It shows an optional flat portion (7) of the shaft. This flat portion can be limited in length, as shown, or extend the full length of the shaft. It provides a tactile indicator allowing the user to orient the shaft by touch alone, without visual inspection. Any unobtrusive tactile indicating means can be used, such as small bumps or dimples. FIG. 7 shows a shape on the shaft end that offers increased fiber mass and improved retention of the swab. A fiber such as Dacron is used to absorb excess fluid and reduce dripping of fluid by the probe. The fiber should be secure on the shaft to avoid depositing of fibers into a wound.

A suggested size range for the shaft is 15 to 20 cm in length and approximately 3 to 3.5 mm in diameter, with the swab and bulb being about 5 mm in diameter. These dimensions are suggested as appropriate for pressure ulcer measurement, but are not required. Some appropriate shaft cross sections are shown herein, but other generally circular, elliptical, or rounded polygonal cross sections can be used. A suggested material for the shaft and bulb is a flexible or semi-flexible plastic. Both ends of the shaft should be rounded for safety. Preferably, the second end of the shaft should have an enlarged bulb (6) as shown in FIGS. 8–13, for improved safety. The bulb can be used as a probe tip at the option of the practitioner. Preferably, tactile indicators are provided, allowing the practitioner to orient the shaft for use of the preferred end and its associated scale quickly by touch, without touching a probe end. An example is shown in FIGS. 10–13, in which a first flat portion (7) exists on the first scale near the first end, and a longer flat portion (8) exists on the second scale (3) starting near the second end (6). With familiarity, a practitioner can automatically orient the device by touch alone, minimizing distraction, and increasing efficiency.

FIGS. 14 and 15 show embodiments of the device with one or two bulb ends respectively, and no swab end. In FIG. 16, two flat portions (7, 8) are provided as tactile indicators. Since both ends are equal, there is no need to swap ends to select a preferred end, so the two flat portions can be equal in length. The flat portions serve here only to orient the scale associated with the end being used. The embodiment of FIGS. 15–16 is suitable for general measurements in medical settings, especially where the practitioner needs to concentrate on a wound or operation without visual distraction. FIG. 17 shows an optional generally triangular cross section for the shaft. In this embodiment, an area differentiated with dimples or the like, near one end of the shaft, is useful for tactile orientation.

For pressure ulcer measurements, the preferred embodiment is FIGS. 8–13, which offers the choice of a swab or bulb end, and includes means to orient the probe for the desired end by touch alone. The practitioner can pick up the device and orient it without looking away from the patient. The surface width and height of an ulcer is measured by placing the scale across the ulcer at two angles about 90 degrees apart. The depths of the ulcer are determined by inserting the probe into the ulcer until it stops against firm flesh, and reading the scale at the skin surface.

Although the present invention has been described herein with respect to a preferred embodiment, it will be understood that the foregoing description is intended to be illustrative, not restrictive. Many modifications of the present invention will occur to those skilled in the art. All such modifications which fall within the scope of the appended claims are intended to be within the scope and spirit of the present invention.

I claim:

1. A pressure ulcer measurement probe, comprising:
    a shaft having a first end and a second end; the first end having a fiber swab; and
    a first metric scale starting at the first end of the shaft;
    whereby the probe can be used for directly measuring the surface dimensions and depths of pressure ulcers.

2. The pressure ulcer measurement probe of claim 1, further comprising tactile means for sensing the orientation of the shaft and scale in the hand by touch.

3. The pressure ulcer measurement probe of claim 2, further comprising a bulb on the second end of the shaft and a second scale starting at the second end of the shaft.

4. The pressure ulcer measurement probe of claim 3, wherein the tactile means comprises first and second flat areas of the shaft, said first and second flat areas covering different portions of the first and second scales respectively.

5. A method for measuring the surface dimensions and depths of a pressure ulcer, comprising the steps of:
    a) placing an elongated measurement probe, having a shaft with an enlarged rounded end and a metric scale starting at said end, across the geometric center of an ulcer surface, with said enlarged end touching the ulcer perimeter at one side of the ulcer;
    b) reading the scale where the shaft crosses the opposite side of the ulcer;
    c) placing the probe across the ulcer approximately perpendicularly to the placement of step a), and reading the scale again as in step b);
    d) Inserting said enlarged end into the ulcer until it stops against firm tissue, and reading the scale at the level of the skin surface to determine the ulcer depth.

6. The method of claim 5, further comprising the initial step of picking up the measurement probe and orienting it in the hand by feeling tactile indicators on the shaft.

7. A pressure ulcer measurement probe, comprising:
    a shaft having a first side, a second side, a first end, a second end, and a midpoint halfway between the first end and the second end;
    a fiber swab on the first end of the shaft;
    a metric scale on the first side of the shaft starting at the first end of the shaft, and
    a metric scale on the second side of the shaft starting at the second end of the shaft,
    whereby the probe can be used for directly measuring the dimensions and depths of pressure ulcers.

8. The pressure ulcer measurement probe of claim 7, further comprising a first tactile indicator on a portion of the first scale, whereby both the scale and the first end of the shaft can be located, and the shaft oriented for use, by touch of the shaft alone, without visual inspection.

9. The pressure ulcer measurement probe of claim 7, further comprising a fiber swab on the second end of the shaft, and a second scale on the shaft starting at the second end of the shaft, whereby the probe can be used equally from either end without turning it around.

10. The pressure ulcer measurement probe of claim 9, further comprising a tactile indicator on the shaft, whereby the scale starting at either end can be located, and the shaft oriented for use equally from either end, by touch of the shaft alone, without visual inspection.

11. The pressure ulcer measurement probe of claim 7, further comprising a bulb on the second end of the shaft, and a second scale on the shaft starting at the second end of the shaft, whereby the probe can be used from either end with a choice of tips.

12. The pressure ulcer measurement probe of claim 11, further comprising a first tactile indicator on a portion of the first scale, and a second tactile indicator on a portion of the second scale, the first and second tactile indicators asymmetric with each other relative to the midpoint of the shaft, whereby a preferred end of the shaft can be distinguished, and its associated scale can be located and oriented for use by touch alone, without visual inspection.

13. The pressure ulcer measurement probe of claim 7, wherein the shaft has a generally triangular cross section with rounded edges.

* * * * *